United States Patent [19]

Powers

[11] Patent Number: 5,207,227
[45] Date of Patent: May 4, 1993

[54] MULTIPROBES WITH THERMAL DIFFUSION FLOW MONITOR

[76] Inventor: Alexandros D. Powers, 2607A S. Walter Reed Dr., Arlington, Va. 22206

[21] Appl. No.: 701,353

[22] Filed: May 10, 1991

Related U.S. Application Data

[63] Continuation of Ser. No. 488,153, Mar. 2, 1990, abandoned.

[51] Int. Cl.⁵ .......................... A61B 5/026; G01F 1/68
[52] U.S. Cl. .................................... 128/691; 128/736; 128/675; 73/202.5; 73/204.16; 73/204.27
[58] Field of Search ............... 128/670, 673, 675, 692, 128/691, 736; 73/202.5, 204.16, 204.17, 204.26, 204.27

[56] References Cited

U.S. PATENT DOCUMENTS

| | | | |
|---|---|---|---|
| 3,789,831 | 2/1974 | Kopaniky et al. | 73/204.16 |
| 4,473,081 | 9/1984 | Dioguardi et al. | 128/670 |
| 4,554,927 | 11/1985 | Fussell | 128/670 |
| 4,660,562 | 4/1987 | House, Sr. | 128/640 |
| 4,688,577 | 8/1987 | Bro | 128/670 |
| 4,787,251 | 11/1988 | Kolodjski | 73/204.19 |
| 4,803,992 | 2/1989 | Lemelson | 128/634 |
| 4,809,704 | 3/1989 | Sogawa et al. | 128/675 |
| 4,815,471 | 3/1989 | Stobie | 128/675 |
| 4,829,819 | 5/1989 | Lefteriou et al. | 73/204.26 |
| 4,841,981 | 6/1989 | Tanabe et al. | 128/692 |
| 4,850,358 | 7/1989 | Millar | 128/637 |
| 4,883,062 | 11/1989 | Micholson Nicholson | 128/667 |
| 4,901,731 | 2/1990 | Millar | 128/675 |
| 4,955,380 | 9/1990 | Edell | 128/635 |
| 4,960,109 | 10/1990 | Lele | 128/736 |
| 4,966,148 | 10/1990 | Millar | 128/675 |
| 4,986,671 | 1/1991 | Sun et al. | 128/675 |
| 5,046,503 | 9/1991 | Schneiderman | 128/692 |

Primary Examiner—Lee S. Cohen
Assistant Examiner—Krista M. Pfaffle
Attorney, Agent, or Firm—Robbins, Dalgarn, Berliner & Carson

[57] ABSTRACT

A single probe with thermal diffusion flow monitor (hereinafter known as "SPTDFM") that has improved reliability, smaller overall size, simpler method of sensor positioning, better compatibility and capability to monitor blood flow, pressure and other critical physiological parameters is provided. The SPTDFM is formed by the combination of a thermal diffusion flow monitor, a pressure monitor, a multiple parameter monitor and a support structure.

26 Claims, 4 Drawing Sheets

MULTIPROBES WITH THERMAL DIFFUSION FLOW MONITOR

This application is a continuation of application Ser. No. 07/488,153, filed Mar. 2, 1990, now abandoned.

BACKGROUND OF THE INVENTION

1. Field of the Invention

The present invention relates to devices which measure tissue blood flow, particularly those based on the thermal diffusion flow concept, measure tissue pressure and can also assess the function of human tissue through the simultaneous monitoring of critical physiological parameters.

2. Description of the prior art

The original reports using the thermal diffusion flow monitor concept appeared in the late 1960's. The work was done by Carter et al. (Carter L. P., Atkinson J. R. "Cortical blood flow in controlled hypotension as measured by thermal diffusion", *J. Neurol. Neurosurg. Psychiatry*, Vol. 36, pp. 906-913, 1973) using a Peltier stack. In order for the Peltier stack to be able to detect flow (as determined by the rate of cooling) the tissue of interest needed to be exposed and uniform contact between the sensor and the tissue surface was required. Although Peltier stacks are widely used, the system suffers from its relatively large size of the sensor and the variability of its output.

Later, in the 1980's, improvements including signal processing to stabilize the sensors output, simplified design of the sensor using a two-point system, where one point is a heat source and the other point a temperature sensor being positioned a short distance away, were made. Still because of its large size, need for visual placement of the probe on the surface of the tissue and unreliable readings due to loose contact of the sensor tip with the surface of the tissue continue to limit its application.

SUMMARY OF THE INVENTION

A single probe with thermal-diffusion flow monitor (hereinafter known as "SPTDFM") that has improved reliability, smaller overall size, simpler method of sensor positioning, better compatibility and capability to monitor blood flow, pressure and other critical physiological parameters is provided.

The MPTDFM of the present invention uses an anemometer and is to be placed into the substance of the tissue itself through a very small surgical opening and does not require visual positioning. The delivery system for the SPTDFM is one that is commonly used in medicine for the placement of various types of monitors, such as pressure monitors. It involves a small skin incision of approximately 1 cm, followed by opening of the connective tissue, such as by drilling a hole in bony coverings as would be require access to the brain, and finally passage of the SPTDFM through this opening into the substance of the tissue. In this manner, the device can be placed quickly at the patient's bedside and a large operative procedure for visual positioning is not required.

In addition, the thermal diffusion flow monitor has better compatibility with pressure monitor as well as multiple parameter monitors in forming SPTDFM for the detection and monitoring of biochemical substances.

Finally, use of an anemometer in the SPTDFM has the advantage of unexpected electrical properties. Specifically, the anemometer can be operated at a constant temperature mode with electrical current being supplied to the sensor. Thus, as the sensor tip of the anemometer is cooled by the blood flowing in the surrounding tissues, electricity will flow to the sensor to adjust it automatically. These changes in electrical current are then directly measured to produce a readout. This direct measurement of the electrical current eliminates the need for additional circuitry that is required by other thermal monitoring designs which measure the temperature difference between a heat source and a temperature monitor.

According to the present invention, a single probe system useful for monitoring blood flow in a tissue is provided. The single probe system comprises a support structure having a first side surface and a second side surface opposite to said first side surface, an anterior and a posterior surface connected to said first and second side surfaces; thermal diffusion means to measure blood flow housed in said support structure near said first side surface, said thermal diffusion means further comprises a conical hot film probe with a sensor tip adapted to contact the tissue, wherein said sensor tip comprises a thin metal layer; a baking material onto which said thin metal layer is deposited; and a protective coating deposited over said thin metal layer; control means to heat said sensor tip as a heat source while simultaneously measuring a temperature correlating to the blood flow in the tissue; pressure monitor means housing in said support structure near said anterior surface and adjacent to said thermal diffusion means to monitor pressure in the tissue; and multiple parameter means housed in said support structure near said second surface and adjacent to said pressure monitor means to monitor oxygen content, temperature and potential of the tissue.

BRIEF DESCRIPTION OF THE DRAWINGS

The novel features which are believed to be characteristic of the invention are set forth with particularity in the appended claims. The invention itself, however both as to its organization and method of operation, may best be understood by reference to the following description taken in connection with the accompanying drawings, wherein similar character refer to similar elements throughout and in which:

DESCRIPTION OF THE PREFERRED EMBODIMENT

Figure 1:
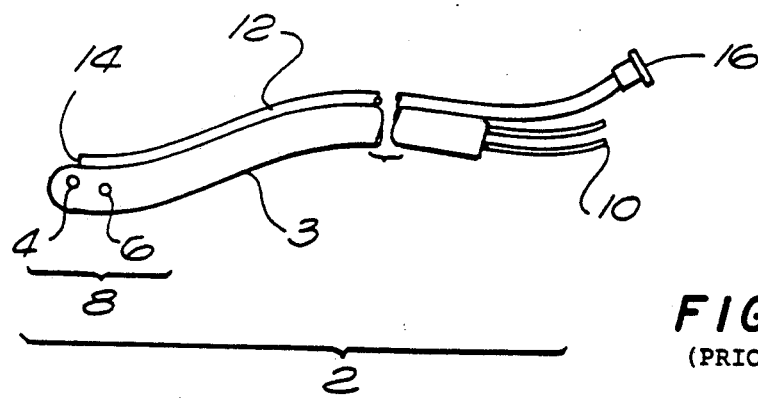
FIG. 1 illustrates a common thermal diffusion blood flow monitor mounted on a support structure.

Referring now to FIG. 1, a common thermal diffusion blood flow probe/pressure monitor 2 mounted on a flexible support structure 3 is shown. The monitor 2 is based on a two-point system where a point 4 is a heat source and another point 6 measures the temperature of the tissue. Together, these two points, 4 and 6, form the sensor tip 8. The sensor tip 8 is placed on the surface of the tissue to be monitored, with both points 4 and 6 requiring intimate contact. The heat source 4 is then activated to a set temperature, generally 41° C., which is higher than the ambient temperature of the underlying tissue. As blood flows past this region, it cools the preheated tissue. Thus, the temperature drop between the two points can be correlated with the rate of regional blood flow. For example, if the measured temperature is 41° C., there is little or no blood flow through the tissue, while a reading of 35° C. means that there is significant blood flow with a high degree of cooling. Since the sensor tips are relatively large, so is the resulting thermal probe having dimensions typically 7 mm (width) by 5 mm (height), including the sensor tip, support structure and wiring. Generally, length of the probe is not of significance as the end of any probe must exit through the skin to be connected to a monitor by current connector 10.

The common thermal diffusion blood flow probe 2 described above can also be used to measure tissue pressure based on the transmission of pressure waves along a tube 12 filled with fluids. One end 14 of the tube 12 is positioned such that it is surrounded by the natural fluids of the tissue. Pressure changes from the tissue are transmitted through the natural fluids, which then are directly transmitted to the fluids at the end of the tube. High tissue pressure causes the natural fluids to flow into the end of the tube, while low tissue pressure will extract fluids out of the end of the tube. This pressure differential causes a displacement of the fluids in the tube, which is then transmitted along the entire length of the tube. By monitoring the opposite end 16 with a pressure transducer, or by measuring the changes in height of the fluid column, a direct pressure is determined. Measurements determined by this method, however, are subject to significant error if the measuring/monitoring end 14 is obstructed with tissue. This is because although solids transmit pressure waves very well, the volume of solid tissue remains fairly constant over a wide range of pressures. Thus, despite wide variations in pressure there will be minimal displacement of fluids by tissue at the end 14 of the tube 12, leading to erroneous pressure determination at the monitoring end 6 of the tube. In contrast, the SPTDFM used in the present invention minimizes and/or eliminates completely this uncertainty in tissue pressure measurements and monitoring.

Figure 2:
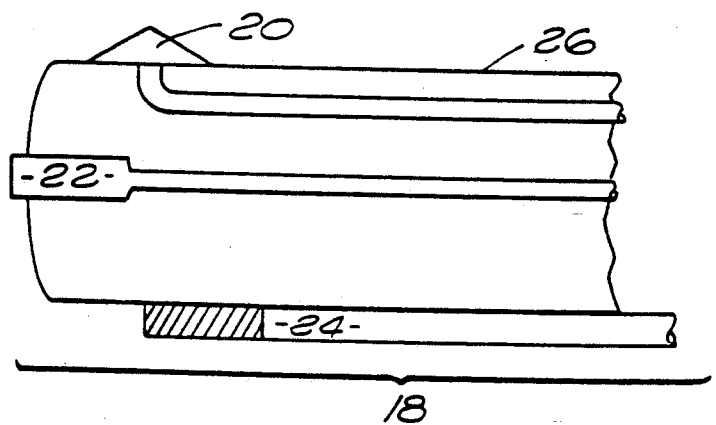
FIG. 2 illustrates an embodiment of the MPTDFM.

FIG. 2 shows an embodiment of the SPTDFM 18 of the present invention. The SPTDFM 18 is formed by the combination of a thermal diffusion flow monitor 20, a pressure monitor 22, a multiple parameter monitor 24 and a support structure 26.

The use of an anemometer to measure the rate of cooling of a solid has not been described before and the anemometer is generally used only when there is a continuous flow of material past the area of measurement (i.e., flowing fluid or stream of air). In addition, the combined use of an anemometer with different modalities in a single monitoring probe has not been commercially produced or experimentally described.

Figure 3:
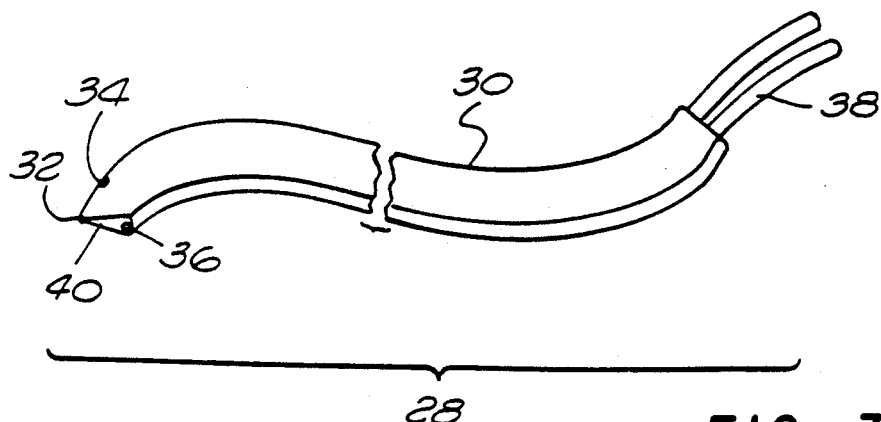
FIG. 3 illustrates a typical conical hot film probe used in the SPTDFM.
Figure 4:
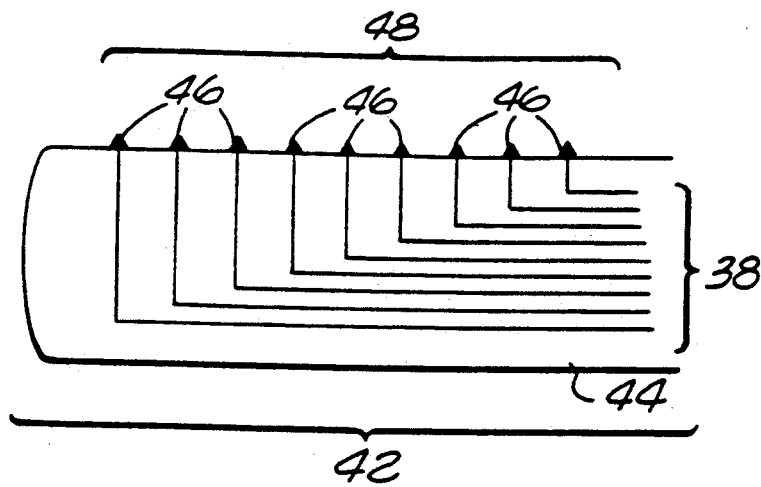
FIG. 4 illustrates one embodiment of the placement of multiple, single-point sensor tips onto a single probe.

The thermal diffusion flow monitor 20 can be in the form of a conical hot film or hot wire probe 28 mounted on a catheter 30 with a diameter of 2 mm (FIG. 3). The probe 28 is a single-point sensor which acts as both a heat source and a temperature monitor. The single point design reduces the size of the sensor tip 32 and also permits multiple sensor tips to be placed onto a single probe (FIG. 4). The sensor 34 of the conical hot film probe is usually made of nickel or platinum deposited in a thin layer onto a backing material 36, such as quartz, and connected to the electronic package by leads 38 attached to the end of the film. Double quartz protective coatings 40 are deposited over the thin film to prevent damage by abrasion or chemical reaction.

In another embodiment, shown in FIG. 4, a single probe 42 with support structure 44 is shown to have multiple sensor tips 46 to simultaneously monitor blood flow at different tissue sites. In addition, the array 48 of sensor tips 46 will more accurately reflect tissue blood flow by minimizing the sampling error associated with measurements made at a single site.

Figure 5A:
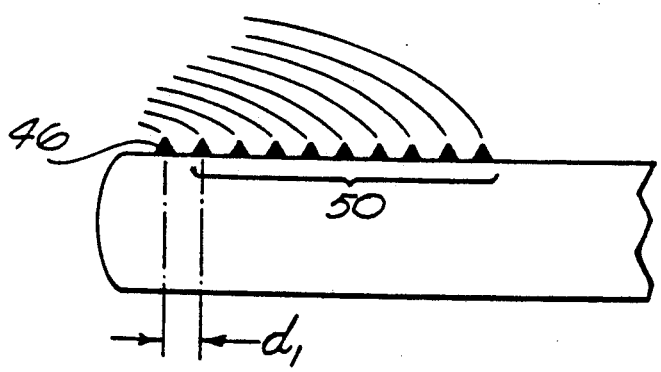
FIGS. 5a-5c illustrate embodiments of temperature gradient monitoring by multiple single-point sensor tips in a single probe.
Figure 5B:
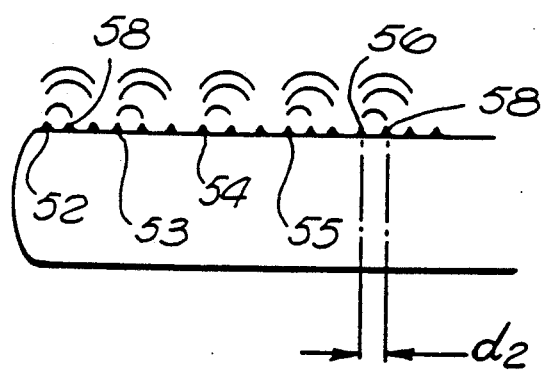
Figure 5C:
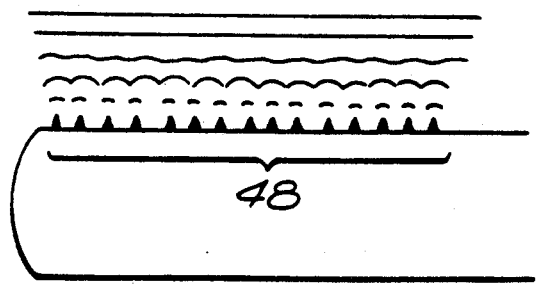

Referring to FIGS. 5a-c, embodiments are shown in which temperature gradients are monitored by periodically altering the function of the single-point sensor tips 46 in the array 48. In one embodiment (FIG. 5a), a single-point sensor tip 46 functions as a heat source. The remaining single-point sensor tips 50 then function as temperature monitors and are used to measure the temperature drop as distance of $d_1$ or multiples thereof $d_1$ increases from that heat source 46 and correlating the temperatures drops to the blood flow in the tissue. In another embodiment (FIG. 5b), several single-point sensor tips 52-56 function as heat sources. The remaining sensors 58 are used to measure temperature drop over the intervening distances and correlating the temperature drops to the blood flow in the tissue. In yet another embodiment (FIG. 5c), the entire array 48 of single-tip sensors are periodically heated. Thus, the array 48 functions as if it were a wire which is being heated and is capable of monitoring its own rate of cooling which correlates to the blood flow in the tissue.

Figure 6A:
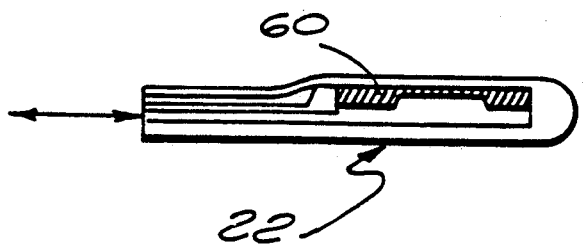
FIG. 6a-6c illustrate embodiments to measure tissue pressure.
Figure 6B:
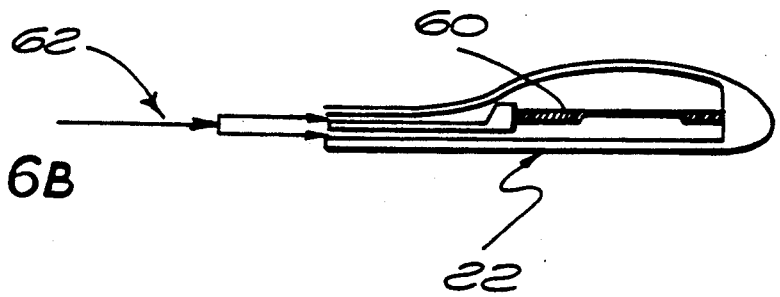
Figure 6C:
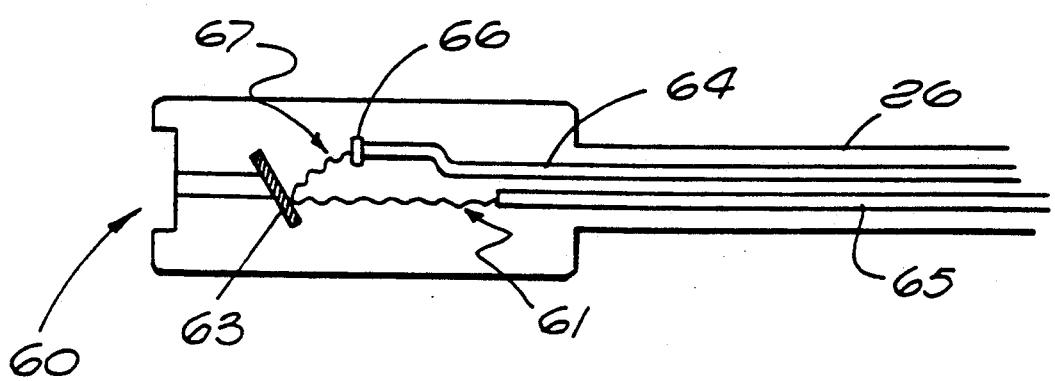

To measure tissue pressure (see FIG. 6a), a pressure transducer 22 with a movable diaphragm and strain gauge 60 is placed in contact with the tissue. As pressure changes are transmitted through the tissue, they will cause a displacement of this diaphragm and strain gauge 60 from its neutral position. The degree of change is then measured by one of two basic methods. In one method (FIG. 6b), a pneumatic circuit 62 connected to the movable diaphragm and strain gauge which pumps air into the pressure transducer 22 is used to counterbalance the tissue pressure causing the diaphragm and strain gauge to return to its neutral position. The pressure used to obtain this equilibrium is measured and directly correlated to the tissue pressure. In the second method (FIG. 6c), a fiber optic cable 64 and a photodetector 66 are used. Initially, when the diaphragm and strain gauge system is in the neutral position, light 61 emitted from a source at one end of fibber optic cable 65, after incidence on a reflective surface 63 connected to the diaphragm 60, is perfectly aligned with the photodetector 66. As tissue pressure changes, the diaphragm 60 is displaced, altering the alignment of the reflective surface 63 and thus the reflected light beam 67 with the photodetector 66. The change in the light intensity measured at the photodetector 66 is transmitted through the sensor cable 64 to a readout. The readout is directly related to tissue pressure. Thus, the thermal diffusion monitors of the present invention can be made fully compatible with various types of pressure monitor systems. For fluid filled cavities, such as ventricles of the brain, it may be advantageous to use a pressure monitor with a fluid filled column.

The multiple parameter monitors used in the present SPTDFM are well-known, and some modification thereof might be utilized without material effect upon the principle of the present invention. It should suffice to indicate that the types of multiple parameter monitor utilized in preferred embodiments of this invention include those temperature, oxygen and potential sensors (TOP Cat. No. M11199-19 probe) produced by Otto-Sensors Corporation, 11000 Cedar Avenue, Cleveland, Ohio 44106.

The support structure 26 for the SPTDFM 18 must be flexible, thermally inert, of a small size while still supporting the placement of multiple sensors and nonallergenic to biological tissues. Materials for the fabrication of the support structure 26 are well-known and include various silicone based materials such as those used for medical catheters.

Figure 7:
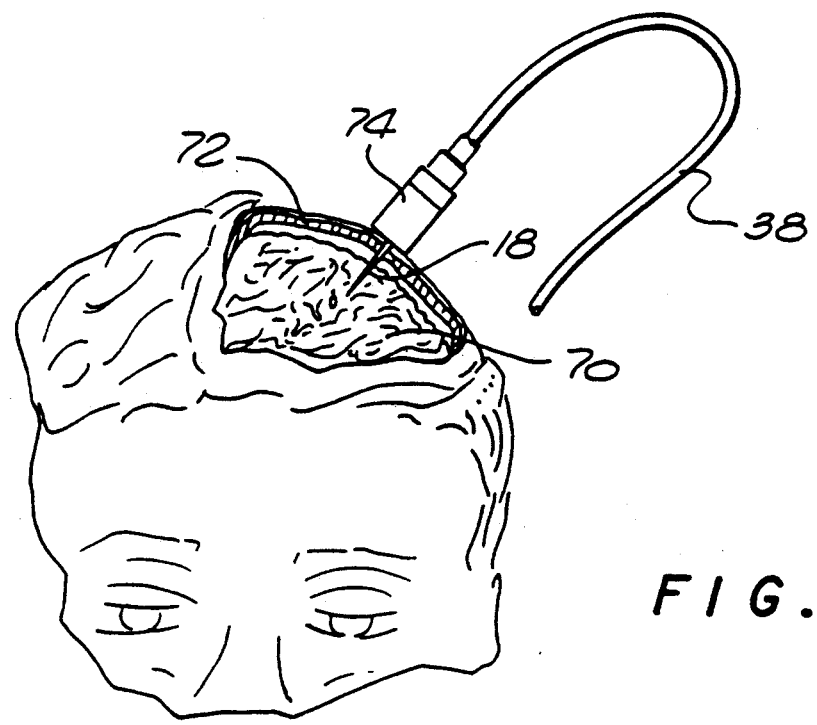
FIG. 7 illustrates one embodiment of the positioning of the SPTDFM probe into the substance of brain tissue.

In operation in one embodiment as shown in FIG. 7, the SPTDFM probe 18 of the present invention is placed into the substance of the tissue (brain) 70 instead of onto the surface of the tissue. The tissues 72 covering the organ-brain are the skin and the bones of the skull. Hollow bolts 74 are used to hold the SPTDFM 18 in a stationary position in the tissue and permit exit of electrical wires 38 for attachment to external electrical components. In other embodiments involving only connective tissues, after the SPTDFM probe 18 is inserted, the tissue can be closed around the probe to provide anchoring instead of the use of bolts 74. Having the probe placed inside the tissue permits an easier method of sensor positioning and also dramatically reduces the chance of a poor contact between the thermal sensor tip 32 and the tissue 70, which is the major source of error with the earlier surface devices.

Figure 8:
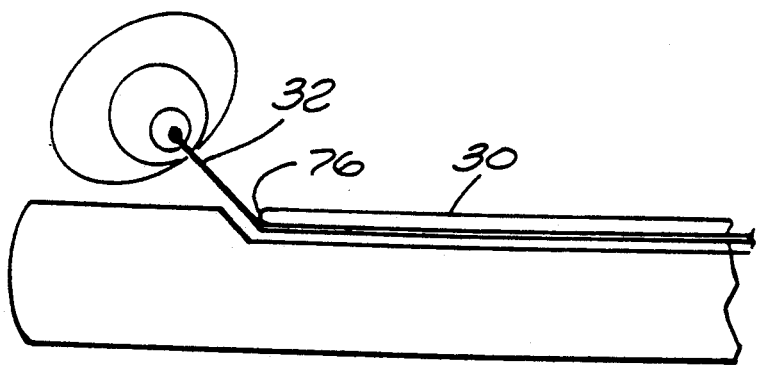
FIG. 8 illustrates one embodiment of the SPTDFM with a side port placed on a catheter.

To provide more accurate readings, by eliminating chemical and thermal interferences from the support structure such as the catheter 30 and to permit the monitoring of a larger amount of tissue, a sensor tip 32 may be advanced through a side port 76 of a suitable catheter 30 (FIG. 8). In this design the sensor tip 32 is in a measuring position, completely surrounded by tissue.

Figure 9:
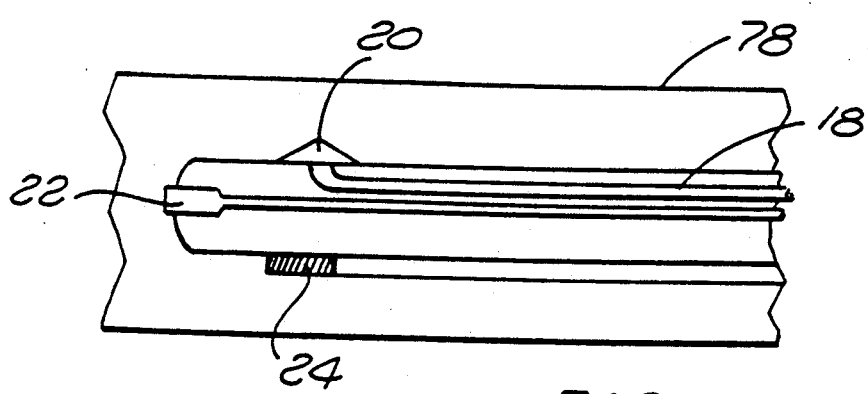
FIG. 9 illustrates an embodiment of the SPTDFM using an introducer.

During insertion of the SPTDFM 18 into the tissue, tissue injury may occur as a result of the physical deformity which takes places as the SPTDFM 18 passes through the organ. This injury will cause the body to mount a localized increase in blood flow, which may lead to inaccurate blood flow determination. To minimize and possibly eliminate this potential error in measurement, an introducer 78 may be used (FIG. 9). The introducer 78 is essentially a cylindrical structure of greater diameter than the SPTDFM 18 itself. The introducer 78 is first inserted into the tissue. Once the introducer 78 is in position, the SPTDFM can be inserted through the center of the introducer. The introducer can then be removed and as the tissue returns to its original position, the SPTDFM sites on the probe will be surrounded.

Those skilled in the art will fully appreciate that the preferred embodiment shown and desirable to illustrate the present invention is exemplary only and that the same principles may be employed in providing a SPTDFM to monitor blood flow and simultaneously monitor pressure and critical physiological parameters. It will be further appreciated that various other modifications or changes, particularly with respect to probe construction, might be made without departing from the gist and essence of the invention. Accordingly, it should be further understood that the invention should be deemed limited only by the scope of the claims which follow and should be interpreted as encompassing all system constructions fairly regardable as functional equivalents of the subject matter to which claims are directed.

Having described our invention, what we claim and desire to secure by letter patent is:

1. A single probe system useful for monitoring blood flow in a tissue comprises:
   a support structure having a first side surface and a second side surface opposite to said first side surface,
   an anterior and a posterior surface connected to said first and second side surfaces;
   thermal diffusion means to measure blood flow housed in said support structure near said first side surface,
   said thermal diffusion means further comprises a conical hot film probe with a sensor tip adapted to contact the tissue, wherein said sensor tip comprises a thin metal layer;
   a backing material onto which said thin metal layer is deposited;
   a protective coating deposited over said thin metal layer;
   control means to heat said sensor tip as a heat source while simultaneously measuring a temperature correlating to the blood flow in the tissue;
   pressure monitor means housed in said support structure near said anterior surface and adjacent to said thermal diffusion means to monitor pressure in the tissue; and
   multiple parameter means housed in said support structure near said second surface and adjacent to said pressure monitor means to monitor oxygen content, temperature and potential of the tissue.

2. The single probe system of claim 1, wherein said pressure monitor means further comprises a pressure transducer having a movable diaphragm and strain gauge that is displaced in accordance with the pressure exerted by the tissue.

3. The single probe system of claim 2, wherein said pressure monitor means further comprises a pneumatic circuit connected to said movable diaphragm and strain gauge to balance the displacement of said diaphragm and strain gauge by the pressure exerted by the tissue.

4. The single probe system of claim 2, wherein said pressure monitor means further comprises a fiber optic photodetector system connected to said movable diaphragm and strain gauge to measure pressure exerted by the tissue;
   said photodetector system comprises:
   a photodetector,
   a light source,
   a fiber optic cable to carry a light from said source onto a reflective surface connected to said movable diaphragm at a first position;
   whereby a first reflected light is reflected from said reflective surface onto said photodetector; and measuring means to measure a change of light intensity at said photodetector when a second reflected light is reflected from said reflective surface when said movable diaphragm is at a second position in accordance with the pressure exerted by the tissue.

5. The single probe system of claim 1, wherein said support structure further comprises a silicone based catheter.

6. The single probe system of claim 5, wherein said catheter further comprises a side port for advancing said thermal diffusion means into the tissue.

7. The single probe system of claim 1, further comprises an introducer surrounding said support structure to reduce inaccuracy in blood flow measurements.

8. A method of monitoring blood flow in a tissue comprising the steps of:
cutting a skin incision of about 1 cm in a protective covering of the tissue;
inserting the single probe system of claim 1 into the tissue;
heating said sensor tip as a heat source while simultaneously measuring a temperature of the tissue and correlating said temperature to blood flow in the tissue.

9. A single probe system useful for monitoring blood flow in a tissue comprises:
a support structure having a first side surface and a second side surface opposite to said first side surface,
an anterior and a posterior surface connected to said first and second side surfaces;
thermal diffusion means to measure blood flow housed in said support structure near said first side surface,
said thermal diffusion means further comprises a conical hot film probe with a plurality of sensor tips adapted to contact the tissue, wherein each sensor tip comprises a thin metal layer;
a backing material onto which said thin metal layer is deposited;
a protective coating deposited over said thin metal layer;
control means to heat a first sensor tip of said plurality of sensor tips as a heat source while simultaneously measuring temperature drops of sensor tips other than said first sensor tip of said plurality of sensor tips at a distance of $d_1$ or multiples thereof from said first sensor tip, and correlating said temperature drops to the blood flow in the tissue;
pressure monitor means housed in said support structure near said anterior surface and adjacent to said thermal diffusion means to monitor pressure in the tissue; and
multiple parameter means housed in said support structure near said second surface and adjacent to said pressure monitor means to monitor oxygen content, temperature and potential of the tissue.

10. The single probe system of claim 9, wherein said pressure monitor means further comprises a pressure transducer having a movable diaphragm and strain gauge that is displaced in accordance with the pressure exerted by the tissue.

11. The single probe system of claim 10, wherein said pressure monitor means further comprises a pneumatic circuit connected to said movable diaphragm and strain gauge to balance the displacement of said diaphragm and strain gauge by the pressure exerted by the tissue.

12. The single probe system of claim 10, wherein said pressure monitor means further comprises a fiber optic photodetector system connected to said movable diaphragm and strain gauge to measure pressure exerted by the tissue;
said photodetector system comprises:
a photodetector,
a light source,
a fiber optic cable to carry a light from said source onto a reflective surface connected to said movable diaphragm at a first position;
whereby a first reflected light is reflected from said reflective surface onto said photodetector; and
measuring means to measure a change of light intensity at said photodetector when a second reflected light is reflected from said reflective surface when said movable diaphragm is at a second position in accordance with the pressure exerted by the tissue.

13. The single probe system of claim 9, wherein said support structure further comprises a silicone based catheter.

14. The single probe system of claim 13, wherein said catheter further comprises a side port for advancing said thermal diffusion means into the tissue.

15. The single probe system of claim 9, further comprises an introducer surrounding said support structure to reduce inaccuracy in blood flow measurements.

16. A method of monitoring blood flow in a tissue comprising the steps of:
cutting a skin incision of about 1 cm in a protective covering of the tissue;
inserting the single probe system of claim 9 into the tissue; and
heating said sensor tip of said plurality of sensor tips as a heat source while simultaneously measuring temperature drops of sensor tips other than said first sensor tip of said plurality of sensor tips at a distance of $d_1$ or multiples thereof from said sensor tip and correlating said temperature drops to the blood flow in the tissue.

17. A single probe system useful for monitoring blood flow in a tissue comprises:
a support structure having a first side surface and a second side surface opposite to said first side surface,
an anterior and a posterior surface connected to said first and second side surfaces;
thermal diffusion means to measure blood flow housed in said support structure near said first side surface,
said thermal diffusion means further comprises a conical hot film probe with a plurality of sensor tips adapted to contact the tissue, wherein each sensor tip comprises a thin metal layer;
a backing material onto which said thin metal layer is deposited;
a protective coating deposited over said thin metal layer;
control means to heat at least two sensor tips of said plurality of sensor tips as heat sources while simultaneously measuring temperature drops of sensor tips other than said first two sensor tips of said plurality of sensor tips at a distance of $d_2$ or multiples thereof from one of said at least two sensor tips, and correlating said temperatures to the blood flow in the tissue;
pressure monitor means housed in said support structure near said anterior surface and adjacent to said thermal diffusion means to monitor pressure in the tissue; and multiple parameter means housed in said support structure near said second surface and adjacent to said pressure monitor means to monitor oxygen content, temperature and potential of the tissue.

18. The single probe system of claim 17, wherein said pressure monitor means further comprises a pressure transducer having a movable diaphragm and strain gauge that is displaced in accordance with the pressure exerted by the tissue.

19. The single probe system of claim 18, wherein said pressure monitor means further comprises a pneumatic circuit connected to said movable diaphragm and strain gauge to balance the displacement of said diaphragm and strain gauge by the pressure exerted by the tissue.

20. The single probe system of claim 19, wherein said support structure further comprises a silicone based catheter.

21. The single probe system of claim 20, wherein said catheter further comprises a side port for advancing said thermal diffusion means into the tissue.

22. The single probe system of claim 18, wherein said pressure monitor means further comprises a fiber optic photodetector system connected to said movable diaphragm and strain gauge to measure pressure exerted by the tissue;

said photodetector system comprises:

a photodetector, a light source, a fiber optic cable to carry a light from said source onto a reflective surface connected to said movable diaphragm at a first position;

whereby a first reflected light is reflected from said reflective surface onto said photodetector; and measuring means to measure a change of light intensity at said photodetector when a second reflected light is reflected from said reflective surface when said movable diaphragm is at a second position in accordance with the pressure exerted by the tissue.

23. The single probe system of claim 17, further comprises an introducer surrounding said support structure to reduce inaccuracy in blood flow measurements.

24. A method of monitoring blood flow in a tissue comprising the steps of:

cutting a skin incision of about 1 cm in a protective covering of the tissue;

inserting the single probe system of claim 17 into the tissue; and heating at least two sensor tips of said plurality of sensor tips as a heat source while simultaneously measuring temperature drops of sensor tips other than said at least two sensor tips of said plurality of sensor tips at a distance of $d_2$ or multiples thereof from one of said at least two sensor tips;, and correlating said temperature drops to the blood flow in the tissue;

25. A thermal diffusion means useful for monitoring blood flow in a tissue comprises:

a conical hot film probe with a plurality of sensor tips adapted to contact the tissue, wherein each sensor tip comprises a thin metal layer;

a backing material onto which said thin metal layer is deposited;

a protective coating deposited over said thin metal layer; and control means to heat a first sensor tip of said plurality of sensor tips as a heat source while simultaneously measuring temperature drops of sensor tips other than said first sensor tip of said plurality of sensor tips at a distance of $d_1$ or multiples thereof from said first sensor tip, and correlating said temperature drops to the blood flow in the tissue.

26. A thermal diffusion means useful for monitoring blood flow in a tissue comprising:

a conical hot film probe with a plurality of sensor tips adapted to contact the tissue, wherein each sensor tip comprises a thin metal layer;

a backing material onto which said thin metal layer is deposited;

a protective coating deposited over said thin metal layer; and control means to heat at least two sensor tips of said plurality of sensor tips as heat sources while simultaneously measuring temperature drops of sensor tips other than said at least two sensor tips of said plurality of sensor tips at a distance of $d_2$ or multiples thereof from one of said at least two sensor tips, and correlating said temperature drops to the blood flow in the tissue.

* * * * *

UNITED STATES PATENT AND TRADEMARK OFFICE
CERTIFICATE OF CORRECTION

PATENT NO. : 5,207,227
DATED : May 4, 1993
INVENTOR(S) : Alexandros D. Powers

It is certified that error appears in the above-indentified patent and that said Letters Patent is hereby corrected as shown below:

On the title page, item [54] and column 1, line 2, change "MULTIPROBES" to --SINGLEPROBES--.

Column 1, line 48, replace "MPTDFM" with --SPTDFM--.

Column 2, line 32, replace "housing" with --housed--.

Column 2, line 52, replace "MPTDFM" with --SPTDFM--.

Column 3, line 54, replace "6" with --16--.

Column 4, line 31, after "thereof", delete "$d_1$".

Column 4, line 37, after "distances", insert --of $d_2$ or multiples thereof--.

Column 4, line 62, replace "fibber" with --fiber--.

Signed and Sealed this

Twenty-ninth Day of March, 1994

Attest:

BRUCE LEHMAN

*Attesting Officer*  *Commissioner of Patents and Trademarks*